(12) United States Patent
Lee

(10) Patent No.: US 9,687,209 B2
(45) Date of Patent: Jun. 27, 2017

(54) INVASIVE DEVICE POSITIONING ASSEMBLY

(71) Applicant: Choon Kee Lee, Denver, CO (US)

(72) Inventor: Choon Kee Lee, Denver, CO (US)

( * ) Notice: Subject to any disclaimer, the term of this patent is extended or adjusted under 35 U.S.C. 154(b) by 274 days.

(21) Appl. No.: 14/511,150

(22) Filed: Oct. 9, 2014

(65) Prior Publication Data

US 2016/0100818 A1  Apr. 14, 2016

(51) Int. Cl.
| | |
|---|---|
| *A61B 8/00* | (2006.01) |
| *A61B 8/08* | (2006.01) |
| *A61B 19/00* | (2006.01) |
| *A61B 17/34* | (2006.01) |

(52) U.S. Cl.
CPC .......... *A61B 8/0841* (2013.01); *A61B 19/201* (2013.01); *A61B 8/4483* (2013.01); *A61B 2017/3413* (2013.01)

(58) Field of Classification Search
CPC ... A61B 8/0841; A61B 8/4218; A61B 8/4272; A61B 8/4483; A61B 17/3403; A61B 2017/3413
See application file for complete search history.

(56) References Cited

U.S. PATENT DOCUMENTS

| | | | | |
|---|---|---|---|---|
| 4,290,309 A | * | 9/1981 | Charlebois | A61B 8/00 73/621 |
| 4,497,325 A | * | 2/1985 | Wedel | A61B 17/3403 408/115 R |
| 4,635,644 A | * | 1/1987 | Yagata | A61B 8/0833 600/464 |
| 5,623,931 A | | 4/1997 | Wung | |
| 5,941,889 A | * | 8/1999 | Cermak | A61B 8/0833 606/130 |
| 6,203,499 B1 | | 3/2001 | Imling | |
| 6,361,499 B1 | * | 3/2002 | Bates | A61B 8/0833 600/461 |
| 6,379,307 B1 | * | 4/2002 | Filly | A61B 8/0833 600/461 |
| 6,475,152 B1 | | 11/2002 | Kelly, Jr. | |
| 6,485,426 B2 | | 11/2002 | Sandhu | |
| 6,546,277 B1 | * | 4/2003 | Franck | A61B 90/10 600/426 |
| 7,635,336 B1 | * | 12/2009 | Pruter | A61B 8/0833 600/461 |
| 7,691,066 B2 | | 4/2010 | Kosaku | |
| 7,837,627 B1 | * | 11/2010 | Pruter | A61B 8/0833 600/461 |
| 7,846,103 B2 | | 12/2010 | Cannon, Jr. | |
| 7,976,469 B2 | | 7/2011 | Bonde | |
| 8,057,487 B2 | | 11/2011 | Chu | |
| 8,073,529 B2 | | 12/2011 | Cermak | |
| 8,118,743 B2 | | 2/2012 | Park | |
| 8,216,149 B2 | | 7/2012 | Oonuki | |
| 8,241,301 B2 | | 8/2012 | Zhang | |

(Continued)

*Primary Examiner* — Matthew F Desanto

(57) ABSTRACT

The present invention presents a positioning assembly to guide an invasive device toward a tissue object of a living body under ultrasonographic visualization. The positioning assembly is a part of an apparatus that controllably introduces an invasive device into a tissue object. The positioning assembly of the present invention is configured to improve on ultrasonographic guidance and to reduce chances of contamination of the apparatus.

5 Claims, 13 Drawing Sheets

(56) References Cited

U.S. PATENT DOCUMENTS

| | | |
|---|---|---|
| 8,257,264 B2 | 9/2012 | Park |
| 8,496,593 B2 | 7/2013 | Park |
| 8,521,257 B2 | 8/2013 | Whitcomb |
| 8,574,160 B2 | 11/2013 | Gorzitze |
| 8,706,186 B2 | 4/2014 | Fichtinger |
| 2002/0058872 A1 | 5/2002 | Steininger |
| 2004/0087851 A1* | 5/2004 | Lee ............... A61B 8/0825 600/407 |
| 2007/0073155 A1* | 3/2007 | Park ............... A61B 8/0833 600/461 |
| 2011/0313293 A1 | 12/2011 | Lindekugel |
| 2012/0059260 A1 | 3/2012 | Robinson |
| 2012/0259220 A1* | 10/2012 | Sheldon ............ A61B 17/3403 600/439 |
| 2012/0259221 A1* | 10/2012 | Sheldon ............ A61B 8/462 600/439 |
| 2013/0066192 A1 | 3/2013 | Sarvestani |
| 2013/0197355 A1 | 8/2013 | Lee |
| 2013/0225984 A1 | 8/2013 | Cheng |

\* cited by examiner

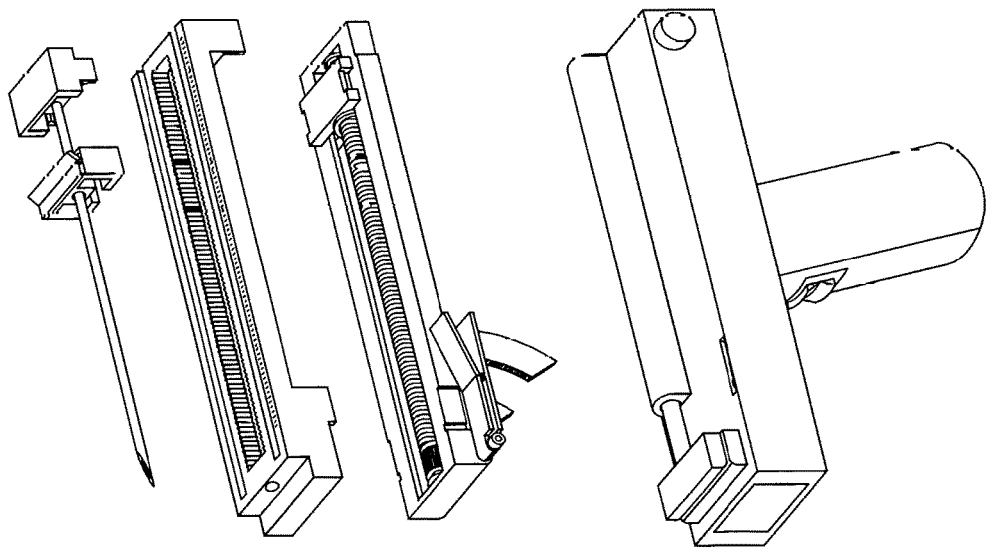

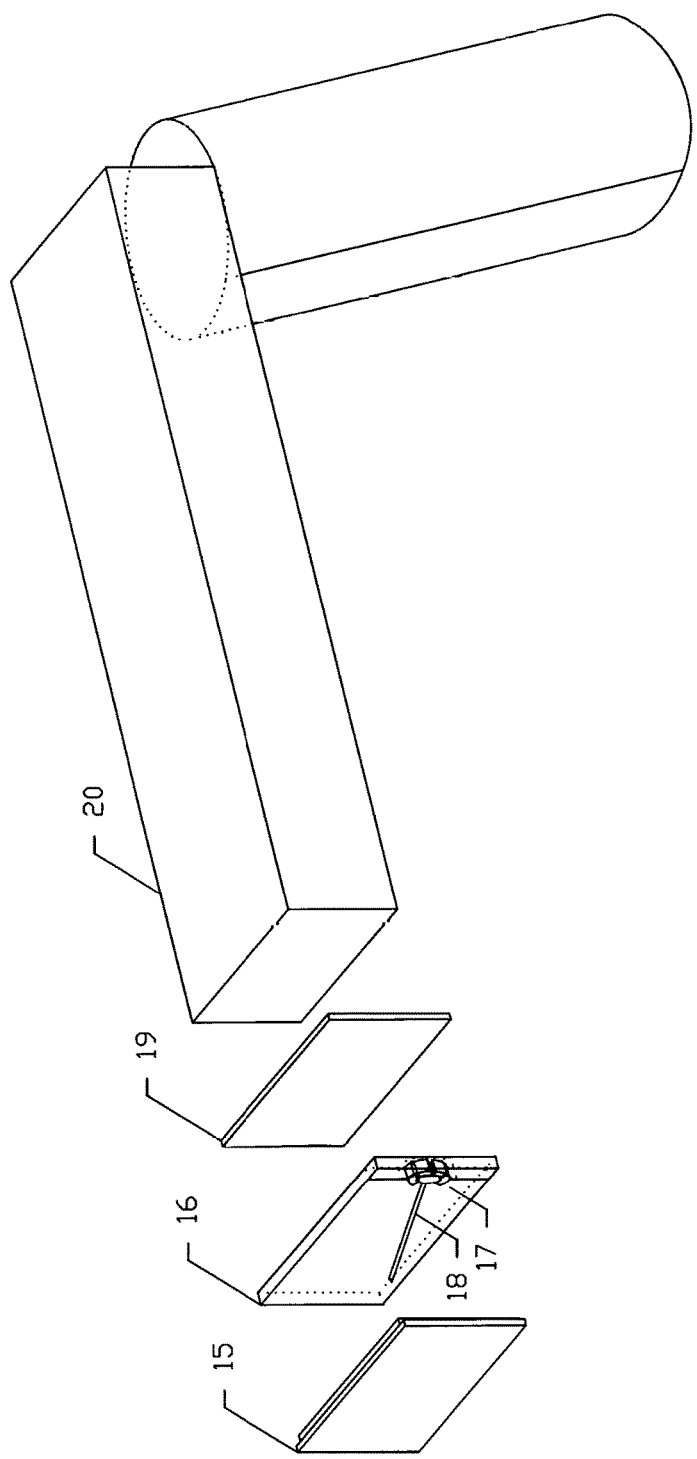

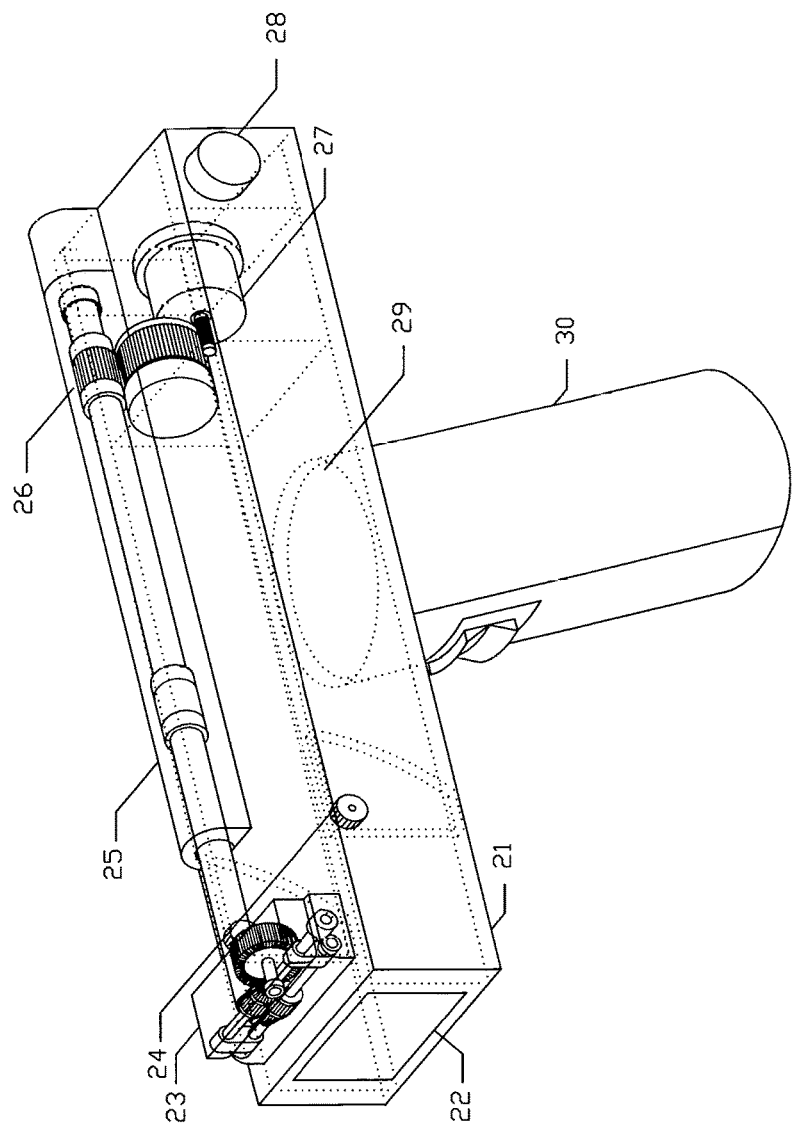

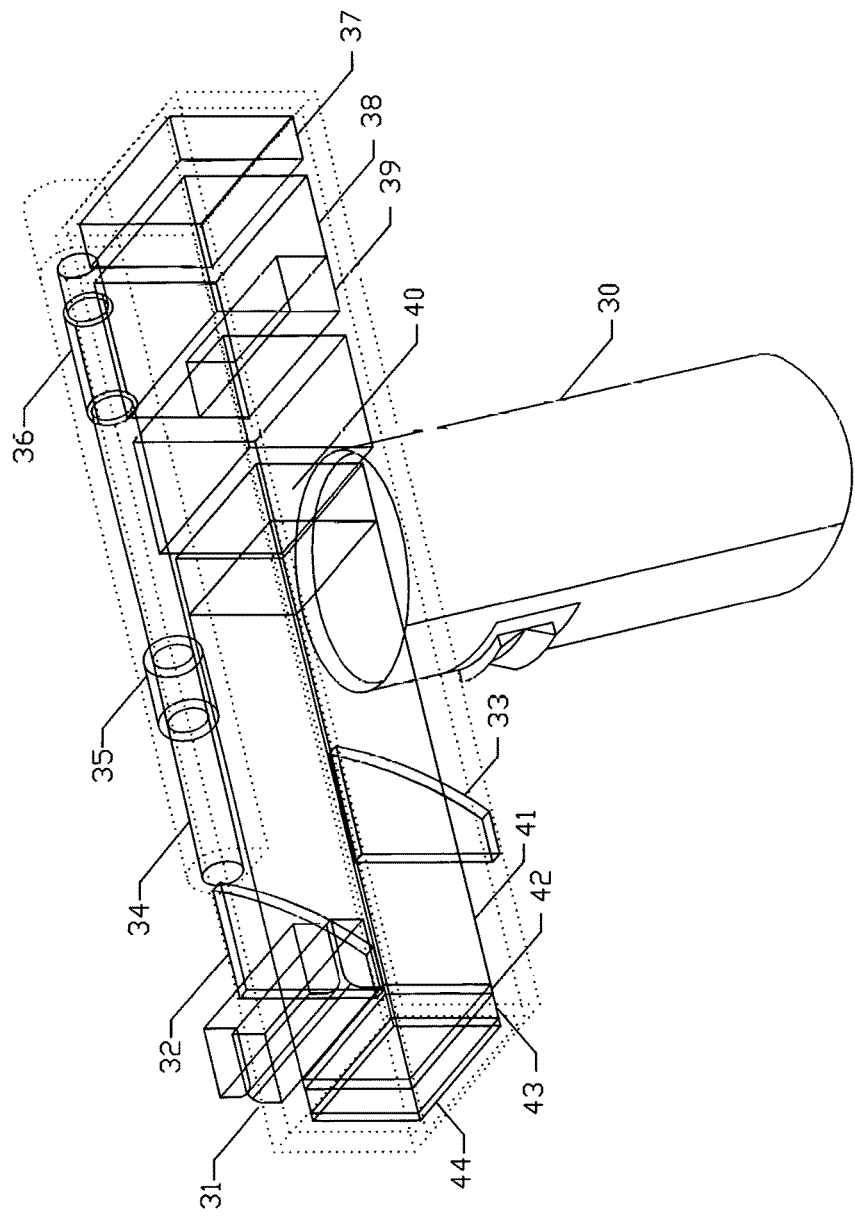

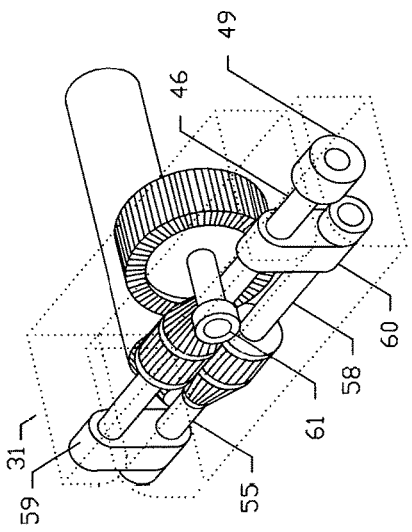
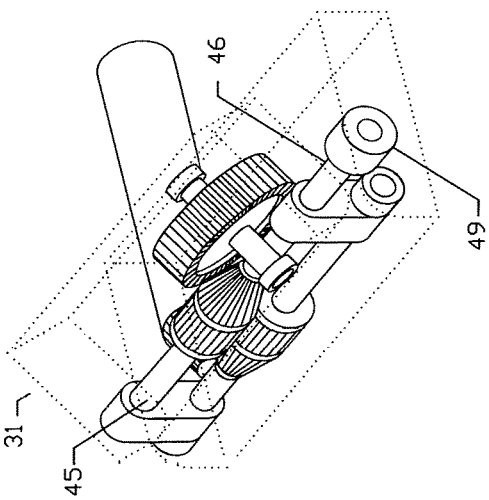
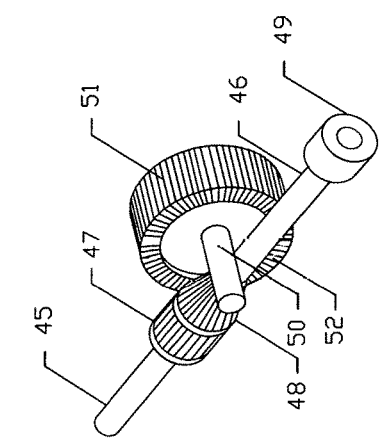
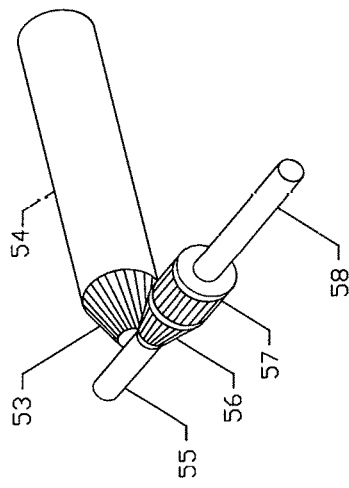

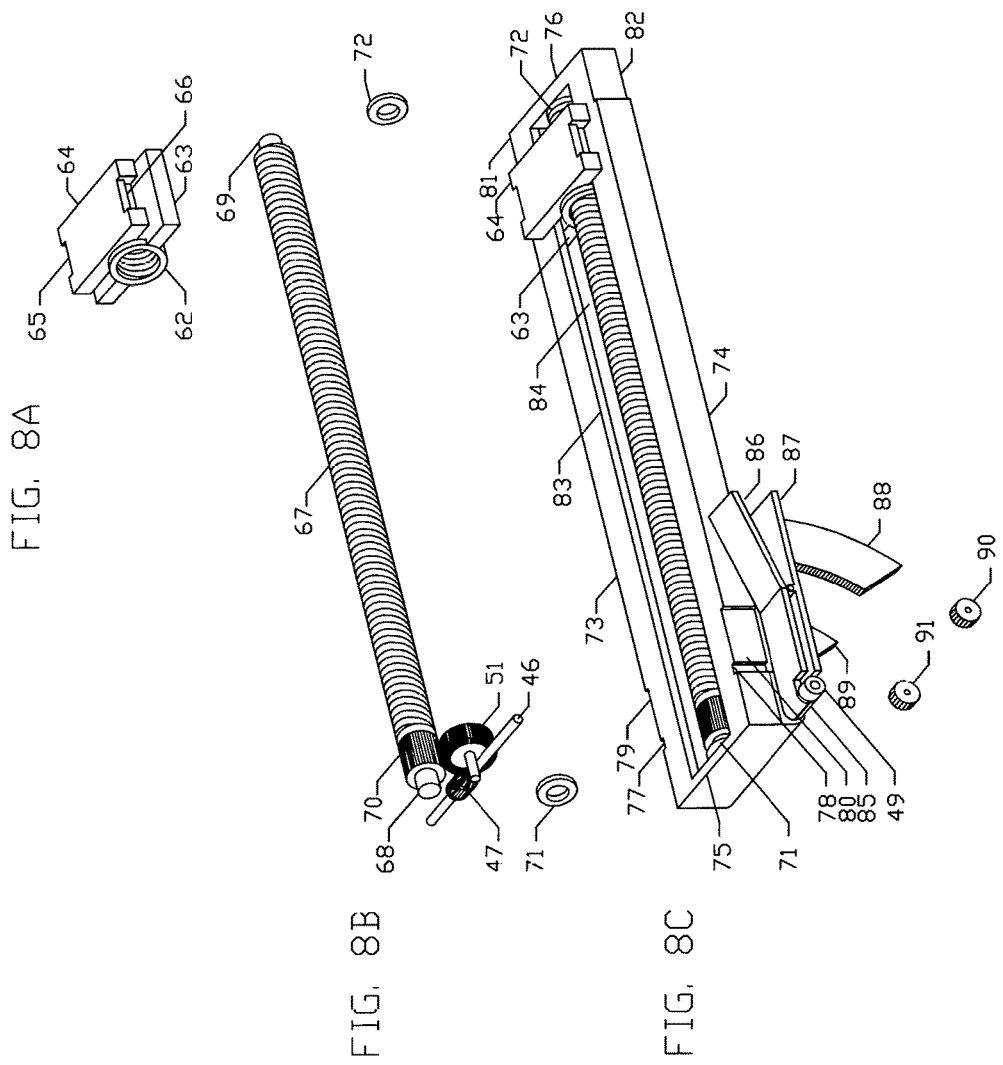

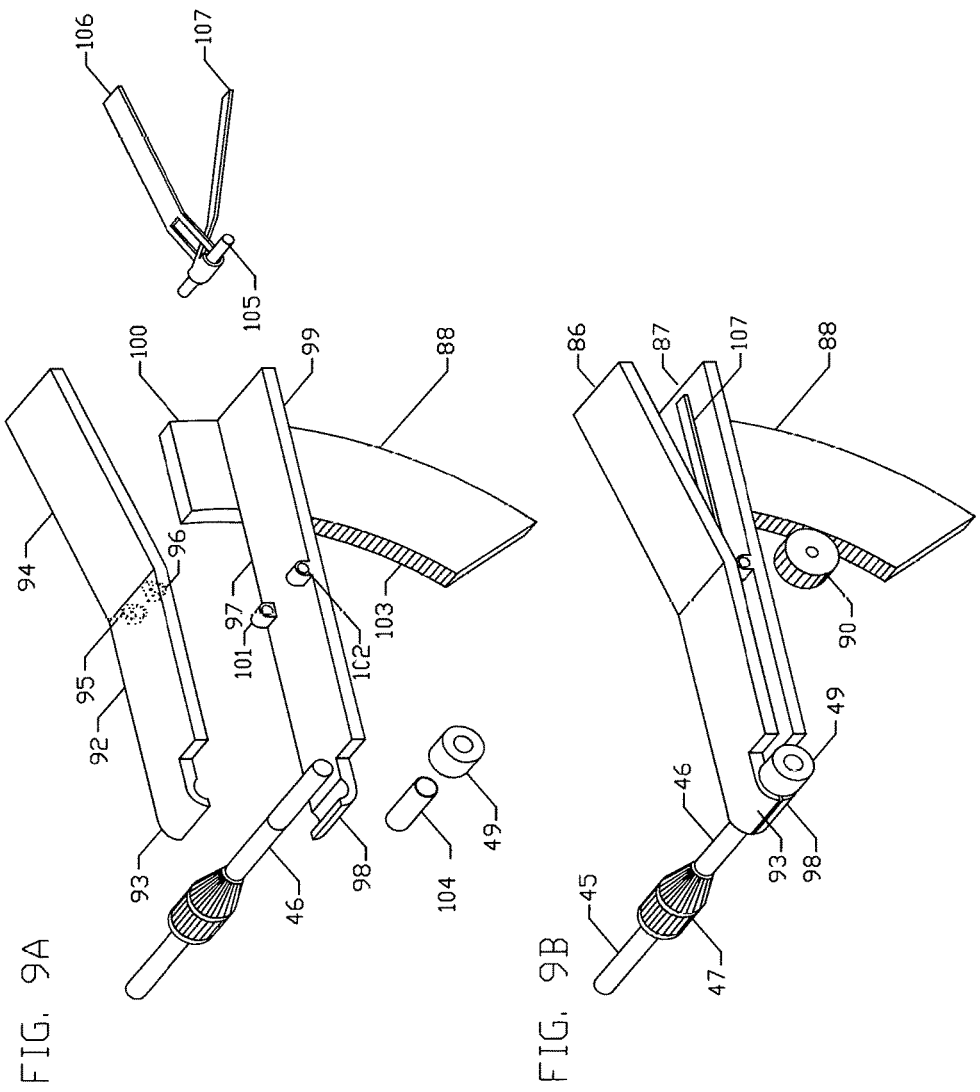

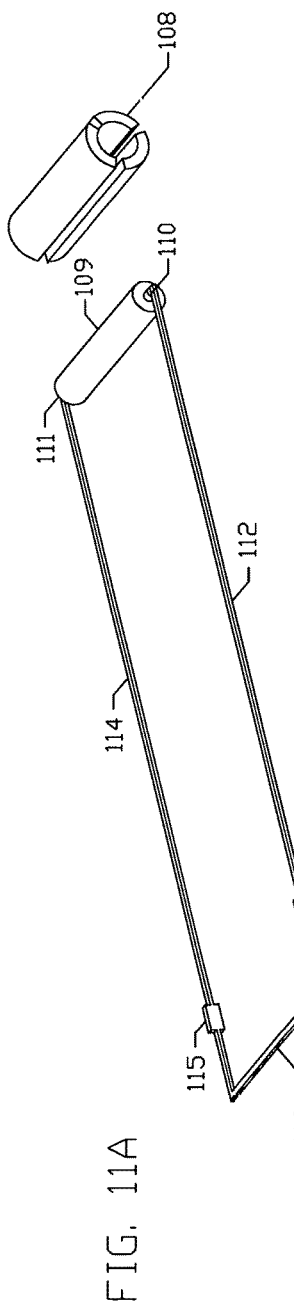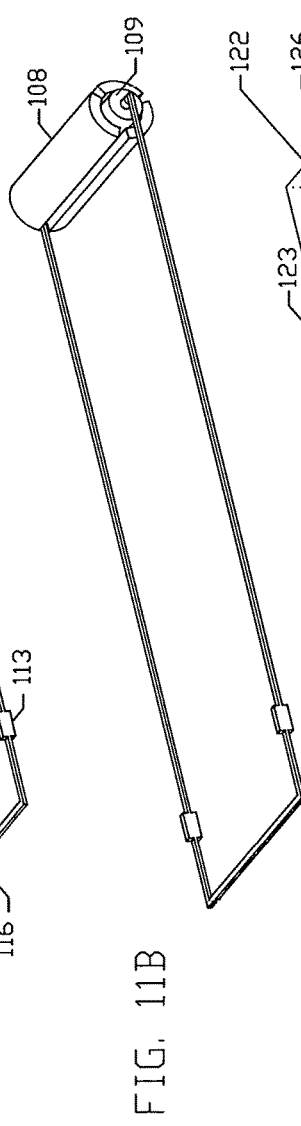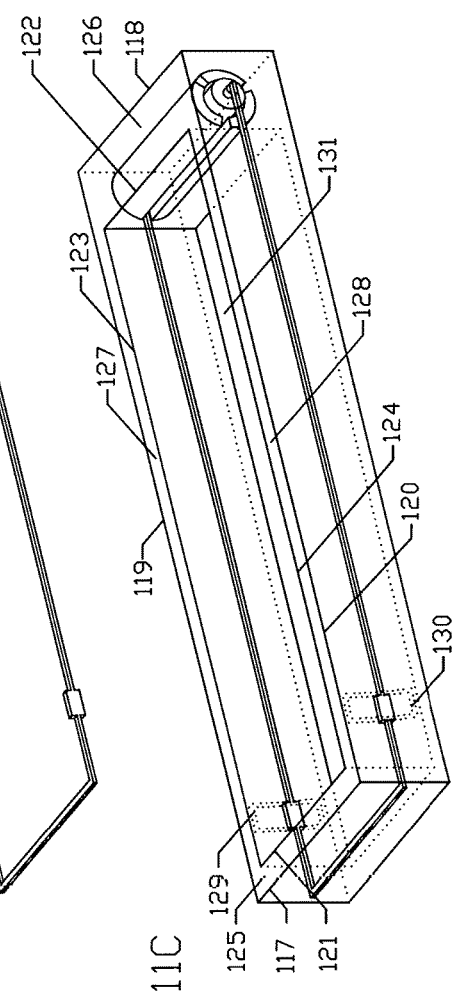

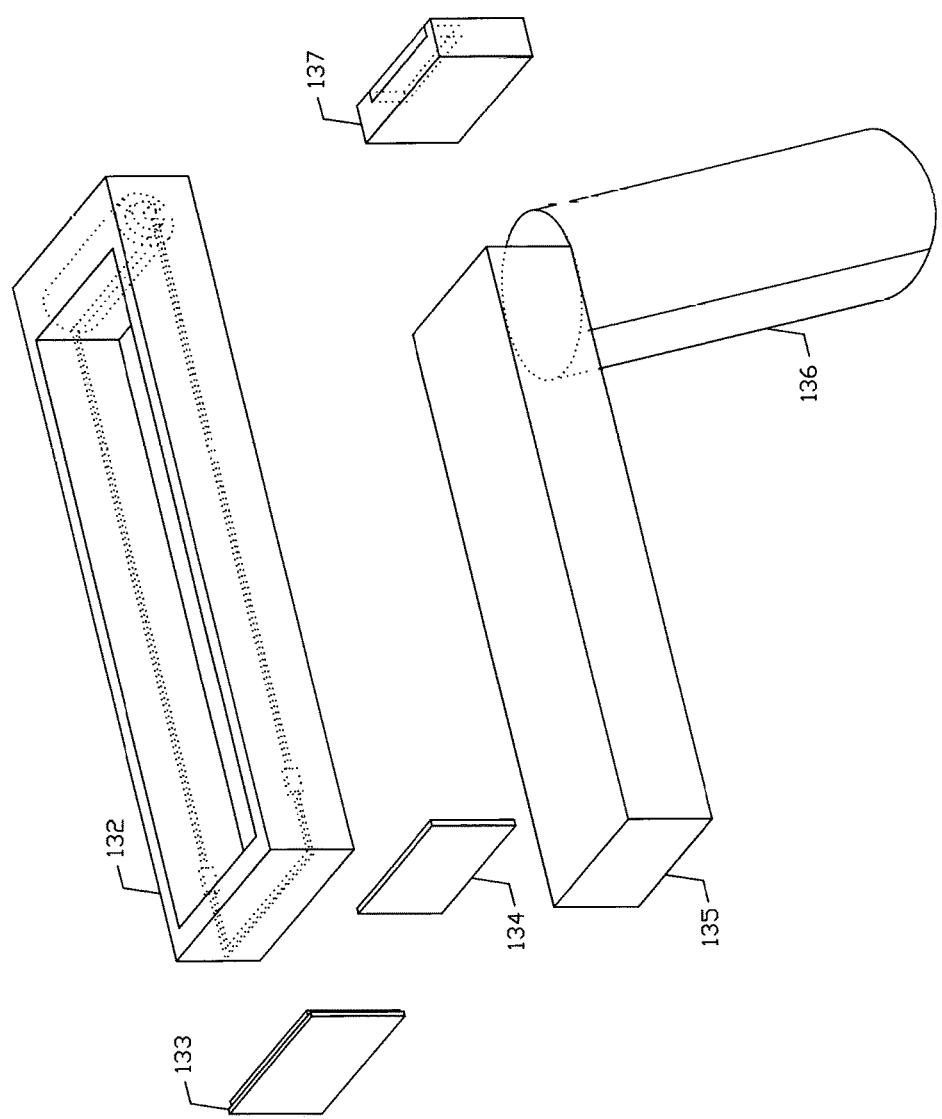

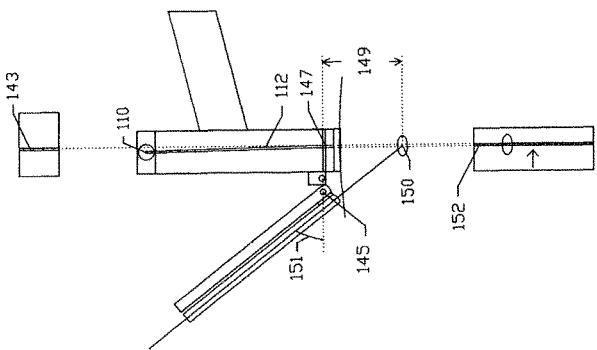
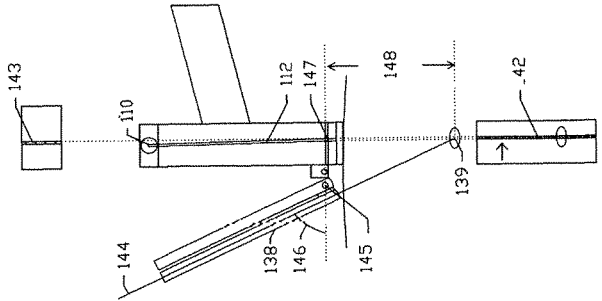
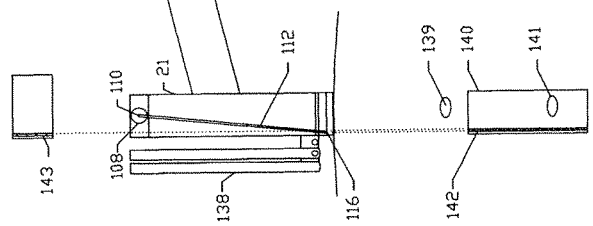

INVASIVE DEVICE POSITIONING ASSEMBLY

TECHNICAL FIELD

The present invention relates generally to the field of introduction of invasive devices to a living body for medical purposes. More specifically, the present invention provides a positioning assembly of an apparatus which stereotactically guides invasive devices under ultrasonographic visualization.

BACKGROUND OF THE INVENTION

In our prior proposed invention (U.S. patent application Ser. No. 14/462,320) for stereotactically guiding an invasive device to reach a tissue object under ultrasonographic visualization, we presented an apparatus that comprises a stereotactic positioning system, a powered propulsion system of an invasive device and a non-reusable invasive device. The apparatus provides in-process visualization of insertion procedures, which uses a trigonometric principle for coordinated angulation of an invasive device with movement of a linear positioning pointer in parallel with a transverse axis of a proximal end of an ultrasound transducer. The linear pointer is a component of an electromagnetic galvanometer-type positioning device that is located in between of the proximal end of the ultrasound transducer and a tissue object under evaluation. The linear pointer indicates a location of a tissue object by a linear shadow line emanating from the ultrasound transducer through the object, distinguished readily from surrounding tissue images. The linear shadow line is produced by the linear pointer blocking a portion of transmissible ultrasound waves generated by the ultrasound transducer toward a tissue object.

An electromagnetic galvanometer-type device comprises a set of electromagnetic windings circumferentially surrounding a pivoting wire core and a linear pointer connected to the pivoting wire core. Upon varying range of electric voltage, current or resistance applied to the electromagnetic galvanometer-type device, the device radially moves a linear pointer as the pivoting wire core rotates inside the electromagnetic windings. One issue of the radial movement of the linear pointer is that it produces oblique presentations to a portion of a linear axis of an ultrasound transducer array. As the majority of ultrasonographic images are generated by volume averaging methods, the oblique placement of the linear pointer in relation to a linear axis of an ultrasound transducer array may limit production of an accurate linear shadow line in an ultrasonographic field. This could produce ultrasonographic artifacts such as comet tail artifacts or side lobe artifacts, which may affect quality of imaging of the linear shadow line adversely.

Trigonometric angulation of an invasive device requires an apex about which the invasive device pivots, and a pivoting means. In our prior proposed invention, a rack and pinion assembly was proposed for pivoting the invasive device. A part of the rack and pinion was configured to be housed inside an ultrasound transducer enclosure. For maintenance of sterility of the apparatus, any opening into a main body of an apparatus increases a risk of contamination of the apparatus by biologic materials and microbial organisms. A sealed-off configuration of an apparatus may reduce chances of contamination of the apparatus and facilitates sterilization of the apparatus without damaging sensitive instruments inside. The sealing-off of the apparatus while allowing unimpeded pivoting of the invasive device about the apex of a trigonometric configuration of the apparatus can be achieved if the pivoting means is isolated from internal components of the apparatus and connected directly to the trigonometric apex for pivoting movements. This configuration obviates a need of placement of a separate pivoting mechanism such as the rack and pinion inside the ultrasound transducer enclosure.

SUMMARY OF THE INVENTION

The present invention provides an invasive device positioning assembly that is configured to align a linear pointer of an electromagnetic galvanometer-type pointing device in parallel with a linear axis of an ultrasound transducer array and to place a pivoting means for an invasive device outside an enclosure housing internal components of an apparatus.

In one embodiment, the present invention is provided as a positioning assembly of an automated apparatus which comprises a propulsion assembly and an invasive device assembly, in addition to the positioning assembly. The positioning assembly encloses an ultrasound transducer and coordinates adjusting an insertion angle of an invasive device with arranging a visualizable linear alignment between a point of a transducer head and a tissue object in an ultrasonographic field. The propulsion assembly, powered by an electric servomotor, converts rotational torque through gear systems to linear to and fro movement for an invasive device and controllably drives the invasive device toward and away from the tissue object. The invasive device assembly releasably carries an invasive device, has a mechanism to limit linear movement of the invasive device and is reversibly anchorable to the propulsion assembly.

In one embodiment, the positioning assembly is provided in one or a plurality of configurations, which comprises a position alignment assembly, a pivoting assembly and a power and electronic control assembly. The positioning alignment assembly comprises an electromagnetic pointing device and a rotary position sensor rotatably mated with the pivoting assembly. Both the electromagnetic pointing device and rotary position sensor are connected to the power and electronic control assembly which coordinates both devices. The rotary position sensor includes potentiometer, optical encoder or magnetic encoder, and is electronically connected to the power and electronic control assembly that relays an electronic information from said position sensor of angular displacements of the propulsion assembly to the electromagnetic pointing device.

In one embodiment, the electromagnetic pointing device is provided in one or a plurality of electromechanical configurations, which is enclosed in a substantially ultrasound-transparent enclosure. The enclosure is provided in one or a plurality of configurations, which includes a rectangular tubular frame. The rectangular tubular frame is made of two transverse rectangular tubular columns and two longitudinal rectangular tubular columns. Both the transverse and longitudinal tubular columns adjoin each other on each proximal and distal end of said rectangular frame, thereby forming a rectangular tubular frame in a way that an inner tubular space of each rectangular tubular column is communicated with an inner tubular space of an adjoining rectangular tubular column. The rectangular tubular frame is sealed off, filled with electrically non-conductive and substantially ultrasound-transparent liquid and leak-proof. The rectangular tubular frame encloses an ultrasound transducer in an open box formed by said rectangular tubular frame and aligns longitudinal and transverse axes of said rectangular tubular frame with longitudinal and transverse axes of the ultrasound transducer, respectively.

In one embodiment, the electromagnetic pointing device is configured as a galvanometer-type device that is provided in one or a plurality of configurations. One of the configurations has a set of semi-circular electromagnetic windings located inside a distal transverse tubular column of the rectangular tubular frame, circumferentially surrounding a pivoting wire core. Both the electromagnetic windings and pivoting wire core are electrically insulated and connected to the power and control assembly. The electromagnetic pointing device uses varying electric voltage, current or resistance to radially move the pivoting wire core inside the electromagnetic windings. A rotating center of an outer circular surface of the pivoting wire core is connected to a longitudinal lever on each side of said pivoting wire core. The longitudinal lever runs longitudinally inside the longitudinal tubular column of the rectangular tubular frame toward a proximal transverse tubular column of said rectangular tubular frame. One end of a linear pointer that blocks off ultrasound waves adjoins a proximal end of the first longitudinal lever and the other end of said linear pointer adjoins a proximal end of the second longitudinal lever running in the opposite tubular column of said rectangular tubular frame. The linear pointer is aligned in parallel with a transverse axis of the proximal transverse tubular column and moves from one side to the other side of said proximal transverse tubular column, driven by radial movement of the pivoting wire core. The proximal transverse tubular column is configured in a flat rectangular shape located proximal to a proximal end of the ultrasound transducer and is substantially ultrasound-transparent. A solid gel couplant is placed in between of an inner wall of the proximal transverse tubular column and a face portion of the proximal end of the transducer, which allows unimpeded transmission of ultrasound waves from the transducer to the proximal transverse tubular column.

In another embodiment, the electromagnetic pointing device is configured to reduce vibrations of the longitudinal levers and the linear pointer inside the rectangular tubular frame. Near the proximal end of both the longitudinal levers, each said longitudinal lever has a vertically curvilinear rail of a certain length projecting in upward and downward directions equidistantly from said longitudinal lever. A corresponding curvilinear slot located in the longitudinal tubular column houses and contacts the curvilinear rail and provides said curvilinear rail with a slidable space. The curvilinear slot is configured to absorb vibrations of the longitudinal lever, including a direct contact means with said longitudinal lever. In this configuration, efficiency of vibration absorption is dependent on contact surface area and contact pressure between said curvilinear rail and said slot.

In one embodiment, the propulsion assembly carrying the invasive device assembly is manually pivotable about a transverse axial hinge located near a proximal end of the apparatus by a pivoting means. The pivoting means is provided in one or a plurality of configurations, which comprises a pivoting handle rotatably encircling the transverse axial hinge and a curvilinear rack and pinion mate. The transverse axial hinge is an extension of an upper transverse axial shaft of the pivotable transverse parallel shaft gear assembly of our prior art, protruding outwardly from one lateral wall of said pivotable transverse parallel shaft gear assembly. The pivoting handle is provided in one or a plurality of configurations including a squeezable clip configuration. The pivoting handle comprises two levers, with a lower lever irreversibly attached to a lower lateral wall of the propulsion assembly and an upper lever connected to the lower lever at a rotatable center of said lower lever. There is provided a spring band slidably placed around the rotatable center, which has two longitudinal planar ends located on an inner surface of a distal portion of both upper and lower levers. The spring band forcefully separates both the upper and lower levers apart as a default position. A proximal portion of both the upper and lower levers is configured to fasten the transverse axial hinge as a default position. There is provided a thin tubular elastomer slidably inserted over the transverse axial hinge, which provides friction on said transverse axial hinge when squeezed by the proximal portion of the pivoting handle, thereby preventing pivoting of the propulsion assembly about the transverse axial hinge unless the distal portion of both the upper and lower levers is squeezed to let the proximal portion open and the transverse axial hinge unfastened. While the distal portion is being squeezed, the pivoting handle can be pivoted about the transverse axial hinge to an intended angle between the longitudinal axis of the ultrasound transducer and a longitudinal axis of the propulsion assembly.

In one embodiment, a pair of symmetrically-arranged curvilinear racks are irreversibly attached to corresponding parts of an undersurface of a bottom of a proximal portion of the propulsion assembly located below each lateral sidewall of said propulsion assembly. One of the two curvilinear racks is also irreversibly attached to the lower lever of the pivoting handle. The curvilinear rack is configured with circumferential teeth located anteriorly and is housed in a corresponding curvilinear slot located inside a lateral sidewall of an ultrasound transducer enclosure. The circumferential teeth of the rack are mated with a pinion located proximal to said teeth inside the curvilinear slot of the lateral sidewall. There are two pinions, one in each curvilinear slot of each sidewall. One pinion is configured to serve as a rotary position sensor and to stabilize curvilinear movement of the rack and the other serves to stabilizes the curvilinear movement of said rack on pivoting movement. The rotary position sensor includes potentiometer, optical encoder or magnetic encoder, and is electronically connected to the power and electronic control assembly that relays an electronic information from said position sensor of angular displacements of the propulsion assembly to the electromagnetic pointing device. Angulation of the propulsion assembly relative to the longitudinal axis of the ultrasound transducer is coordinated with ultrasonographically visualizable pointing of a tissue object in an ultrasonographic view by manual pivoting of the propulsion assembly about the transverse axial hinge of the proximal portion of said propulsion assembly. The pair of racks located under both the lateral sidewalls passively move in and out of the corresponding curvilinear slots of the ultrasound transducer enclosure.

In one embodiment, powering up and controlling the position alignment assembly is provided by the power and electronic control assembly which comprises an integrated circuit board, a control knob connected to the integrated circuit board and a power source. The power and electronic control assembly is located distally to the rectangular tubular frame enclosing the electromagnetic pointing device and electronically connected to the position alignment assembly. A compartment for replaceable batteries is located in the power and electronic control assembly and connects batteries electrically with the integrated circuit board and the position alignment assembly.

BRIEF DESCRIPTION OF THE DRAWINGS

FIG. 1 shows a schematic example of individual components of the apparatus: FIG. 1A shows a schematic illustration of an example of an invasive device; FIG. 1B shows an invasive device frame; FIG. 1C shows a propulsion assembly; FIG. 1D shows a principal enclosure attached to a handle.

In FIG. 2.

FIG. 3 shows a schematic illustration of a prior art of an example of individual parts of a gear arrangement of a pivotable transverse parallel shaft gear assembly.

FIG. 4 shows a schematic example of a prior art of components housed in the principal enclosure including a galvanometer-type electromagnetic pointing device.

FIG. 5 shows a schematic example of individual components of gear arrangements in and around the principal enclosure of the present invention.

FIG. 6 shows a schematic example of the present invention illustrating individual compartments of the principal enclosure, the output shaft enclosure, the pivotable transverse parallel shaft gear assembly, a pair of open slots for rack and pinion gears and the handle.

FIG. 7 shows a schematic illustration of an example of individual parts of a gear arrangement of the pivotable transverse parallel shaft gear assembly of the present invention: FIG. 7A represents an upper transverse shaft gear assembly; FIG. 7B shows a lower transverse shaft gear assembly; FIG. 7C shows arrangement of the pivotable transverse parallel shaft gear assembly in a pair of parallel shaft gear mounts; FIG. 7D shows an angulated upper transverse parallel shaft gear assembly.

FIG. 8 shows a schematic example of individual components of the propulsion assembly of the present invention; FIG. 8A shows a propulsion assembly; FIG. 8B shows a longitudinal helical gear shaft; FIG. 8C shows a longitudinally rectangular frame.

FIG. 9 illustrates a schematic example of individual components of a pivoting handle of the present invention; FIG. 9A shows an exploded view of the pivoting handle; FIG. 9B shows a fully assembled pivoting handle.

FIG. 10 shows a schematic example of angulation of the propulsion assembly of the present invention.

FIG. 11 shows a schematic illustration of an example of a galvanometer-type electromagnetic pointing device of the present invention; FIGS. 11A and 11B show a set of semicircular electromagnetic windings circumferentially surrounding a pivoting wire core; Figure FIG. 11C illustrates a placement of the galvanometer-type electromagnetic pointing device enclosed inside a rectangular tubular frame.

FIG. 12 depicts a schematic illustration of components housed in the principal enclosure of the present invention.

FIG. 13 depicts a schematic illustration of an example of a method of coordination of an angular rotation of the invasive device assembly with a linear movement of a linear pointer of the invasive device positioning assembly to aim at a tissue object.

DETAILED DESCRIPTION OF THE DRAWINGS

As described below, the present invention provides an improved positioning assembly guiding an invasive device to a tissue object and methods of use. It is to be understood that the descriptions are solely for the purpose of illustrating the present invention, and should not be understood in any way as restrictive or limited. Embodiments of the present invention are preferably depicted with reference to FIGS. 1 and 5 to 13, however, such reference is not intended to limit the present invention in any manner. The drawings do not represent actual dimension of devices, but illustrate the principles of the present invention.

FIG. 1 shows a schematic illustration of an example of the apparatus according to the present invention. FIG. 1A represents an invasive device; FIG. 1B represents an invasive device frame; FIG. 1C represents a propulsion assembly with a pivoting handle attached to a lateral sidewall of said propulsion assembly; FIG. 1D shows a principal enclosure with associated assemblies. The invasive device of 1A is slidably insertable into the invasive device frame of 1B through an open distal end of said invasive device frame. The invasive device assembly comprising both the 1A and 1B is releasably attachable to the propulsion assembly of 1C. The propulsion assembly of 1C is assembled with the 1D and is pivotable at a proximal end of said propulsion assembly.

Figure 2A:
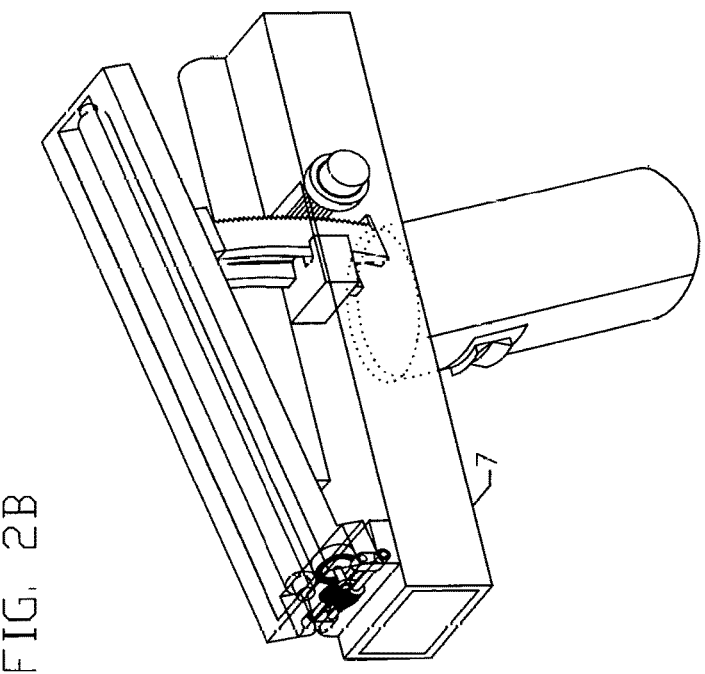
FIG. 2A shows a schematic example of a prior art of the propulsion assembly with a rack and pinion assembly and FIG. 2B illustrates an example of a pivoted propulsion assembly by the rack and pinion assembly.
Figure 2B:
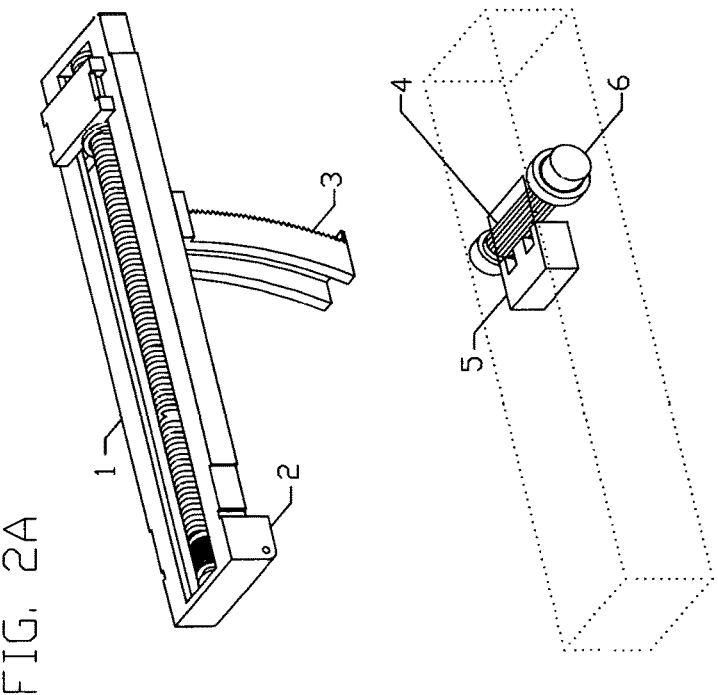

FIG. 2 shows a schematic example of a prior art of the propulsion assembly. FIG. 2A shows a main frame 1 and the proximal end 2 of the propulsion assembly. A vertically curvilinear rack 3 is irreversibly attached to an undersurface of the propulsion assembly, which mates with a pinion 4 located inside the principal enclosure. The rack 3 is guided by a rack stabilizer 5 for curvilinear movements and is driven by rotation of a knob 6 of the pinion 4. FIG. 2B illustrates an example of a pivoted propulsion assembly by the rack and pinion assembly, a part of which is operably housed in the principal enclosure 7.

Figure 3A:
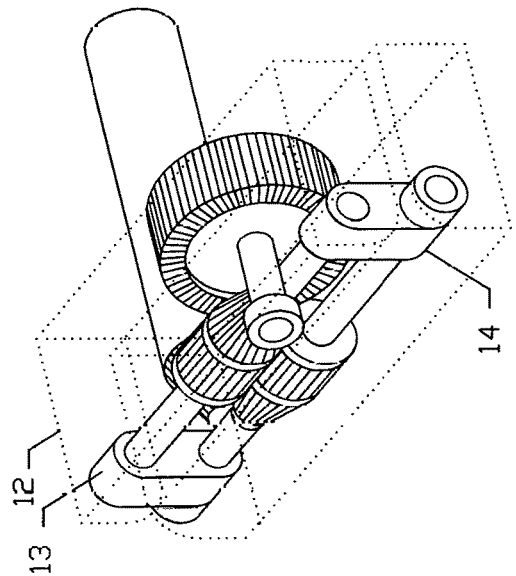
FIG. 3A represents an upper transverse shaft gear assembly.
Figure 3B:
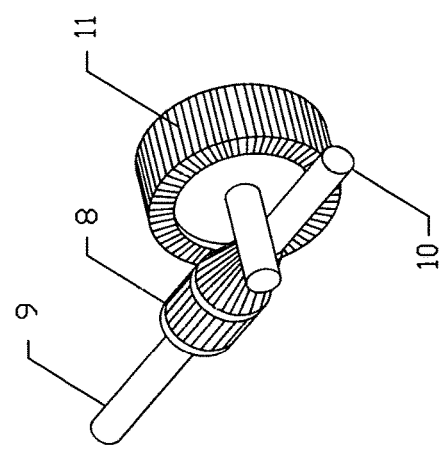
FIG. 3B shows the pivotable transverse parallel shaft gear assembly encased in a pair of parallel shaft gear mounts.

FIG. 3 shows a schematic illustration of a prior art of an example of individual parts of a gear arrangement of a pivotable transverse parallel shaft gear assembly: FIG. 3A represents an upper transverse shaft gear assembly having an axial shaft 9 fixedly attached to a transverse shaft gear 8. The transverse shaft gear 8 is fixedly connected to an axial shaft 10 on the other side and is configured to mate with a longitudinal cylindrical gear complex 11. Both the transverse shaft gear assembly and longitudinal cylindrical gear complex are housed in an upper gearbox 12. Both the transverse shafts 9 and 10 of the transverse shaft gear assembly are rotatably secured in parallel shaft gear mounts 13 and 14, respectively.

FIG. 4 shows a schematic example of a prior art of components housed in the principal enclosure including a galvanometer-type electromagnetic pointing device. A non-reusable solid gel couplant 15 is placed in front of an electromagnetic pointing device 16 and a second solid gel couplant 19 is placed in between of the electromagnetic pointing device 16 and an ultrasound transducer 20. The solid gel couplant 15 contacts with a skin overlying a tissue object and the couplant 19 facilitates transmission of ultrasound waves between the ultrasound transducer 20 and the electromagnetic pointing device 16. The electromagnetic pointing device 16 is configured as a substantially ultrasound-transparent flat rectangular box, which comprises a rotatable center 17 having a pivoting wire core and electromagnetic windings and a linear pointer 18 attached to said rotatable center 17. The flat rectangular box is located proximal to a face of the transducer, which is filled with one or a plurality of type(s) of substantially ultrasound-transparent liquid and leak-proof. The galvanometer-type electromagnetic pointing device uses varying range of electric voltage, current or resistance to radially move the linear pointer 18 around the rotatable center 17.

FIG. 5 shows a schematic example of an overview of gear arrangements enclosed in and attached to the principal enclosure 21 according to the present invention. The proximal end 22 of said enclosure is configured as an open window which ultrasound waves pass through and which encloses ultrasound gel couplants and an electromagnetic pointing device. On an upper wall of a proximal portion of the principal enclosure 21, a pivotable transverse parallel shaft gear assembly 23 is attached to an outer surface of said upper wall. Inside a proximal lateral sidewall of the principal enclosure 21 on each side, there is provided an open space in which a pinion 24 is rotatably located. Near a distal portion of the principal enclosure 21, a servomotor and gearbox assembly 26 having a rotating axis of the servomotor 27 is arranged longitudinally. The servomotor and gearbox assembly 26 is connected to a distal portion of a longitudinal output shaft enclosure 25 which is attached to one longitudinal side of the upper wall of the principal enclosure 21 and encloses a longitudinal output shaft. A tubular handle assembly 30 is attached to an open mid portion 29 of a lower wall of the principal enclosure 21. A rotatable knob 28 is attached to a distal lateral sidewall, which provides a power and electronic control assembly with digitized numerical information.

FIG. 6 based on the present invention shows a schematic see-through illustration of an example of individual compartments of the pivotable transverse parallel shaft gear assembly, the output shaft enclosure and the principal enclosure. Referring to FIG. 5, a couple of compartments 31 for the pivotable transverse parallel shaft gear assembly are provided, which is attached to the upper wall of the principal enclosure 21. Longitudinally distal to the pivotable shaft gear assembly compartments, a pair of open vertical slots 32 and 33 are provided in one or a plurality of configurations, which are carved inside lateral sidewalls of the principal enclosure through which a pair of corresponding racks slide vertically. The vertical slot is separated from an inner space of the principal enclosure and is open on both top and bottom portions. The open configuration allows washing and contact sterilization of the principal enclosure without affecting inner components of said principal enclosure.

The output shaft enclosure of FIG. 6 comprises an output shaft housing 34, a housing 35 for a rolling-element bearing portion of the output shaft and an output shaft gear housing 36. A bottom of the output shaft gear housing 36 is open to an upper part of the servomotor and gearbox compartment 38 to allow meshing of the output shaft gear with a gear of the gearbox. At the distal portion of the principal enclosure, there is provided a compartment 37 for an electronic control assembly behind the servomotor and gearbox compartment 38. Inside said servomotor and gearbox compartment 39, there is provided a battery compartment 39. The proximal portion of the principal enclosure 21 is provided in one or a plurality of configurations, including serially arranged rectangularly tubular compartments 42 and 44 to reversibly hold a pair of solid gel couplants to enhance ultrasound transmission between a face of the transducer and a tissue, and another rectangularly tubular compartment 43 located in between of the compartments 42 and 44 to house a proximal portion of an electromagnetic pointing device. A distal portion of the electromagnetic pointing device is located in a compartment 40 longitudinally distal to a compartment 41 for an ultrasound transducer. The compartment 41 is open below to a tubular space of the handle assembly 30 attached to the mid portion of the lower wall of said enclosure 21.

FIG. 7 shows a schematic illustration of an example of individual parts of a gear arrangement of the pivotable transverse parallel shaft gear assembly of the present invention. As illustrated in FIG. 7A, an upper transverse parallel shaft gear comprises a transverse spur gear 47 fixedly inserted over a transverse axial shaft 45 and a transverse bevel gear 48 coaxially combined with said transverse spur gear 47. The other end of the transverse bevel gear 48 is fixedly connected to an elongated transverse axial shaft 46 which serves as a hinge. A circular flange 49 caps a free end of the transverse axial shaft 46. The upper transverse parallel shaft gear meshes at a right angle with a longitudinal cylindrical gear complex having a planar bevel gear 52, a cylindrical spur gear 51 on an outer cylindrical surface and a longitudinal shaft 50. The planar bevel gear 52 is projected from a plane perpendicular to the longitudinal shaft 50 of the longitudinal cylindrical gear complex. The transverse bevel gear 47 meshes at a right angle with the corresponding planar bevel gear 52.

FIG. 7B shows a lower transverse shaft gear assembly which comprises a transverse spur gear 57 fixedly inserted over a transverse axial shaft 58, a transverse bevel gear 56 coaxially combined with said transverse spur gear 57 and a longitudinal bevel gear 53 located at a proximal end of the output shaft 54. One end of the transverse bevel gear 56 is fixedly connected to a transverse axial shaft 55. The transverse bevel gear 56 is configured to mesh at a right angle with the longitudinal bevel gear 53. FIG. 7C shows the pivotable transverse parallel shaft gear assembly encased in a pair of parallel shaft gear mounts 59 and 60. Both the parallel shaft gear mounts 59 and 60 are fixedly attached to a lower gearbox and maintain a vertically stacked-up meshing configuration of both the lower and upper transverse shaft gear assemblies. The parallel shaft gear mounts 59 and 60 are configured to have a rolling-element bearing joint for each end of said shaft to reduce rotational friction of said shafts inside said shaft gear mounts. Referring to FIG. 7A, the longitudinal shaft 50 is encased in a flange 61 which is configured to have a rolling-element bearing joint to reduce rotational friction of said shaft 50. The elongated transverse axial shaft 49 is configured to penetrate through one lateral sidewall of a upper gearbox of the gearbox 31 and to protrude for a certain length from an outer surface of the lateral sidewall. The end of the elongated transverse axial shaft is anchored by the flange 49. FIG. 7D shows a pivoted upper gearbox enclosing the upper transverse parallel shaft gear assembly about the transverse axial shafts 45 and 46. A position of a transverse axis of the transverse axial shaft 46 relative to a transverse axis of the lower gearbox remains unchanged during pivoting movement of the upper gearbox.

FIG. 8 shows a schematic example of individual components of the propulsion assembly of the present invention. In one example, the propulsion assembly comprises a propulsion block in an overtube configuration depicted in FIG. 8A, a longitudinal helical gear shaft in FIG. 8B and a longitudinally rectangular frame 73 in FIG. 8C. The propulsion block of FIG. 8A comprises a longitudinal overtube 62 having internal threads on an inner wall of said overtube, a pair of lower horizontal slide rails 63 with said each slide rail axially attached to each opposite side of an outer tubular wall of said overtube 62 and an upper slide rail 64 vertically stacked up on an upper part of said overtube 62. The upper slide rail 64 has a pair of notches 65 and 66 along longitudinal lateral edges of said slide rail 64. A longitudinal shaft limited by a proximal rotating shaft 68 and a distal rotating shaft 69 in FIG. 8B comprises a longitudinal spur gear 70 on a proximal outer surface of said shaft and a helical gear shaft 67 which has a continuous helical gear on an outer surface of said shaft between a distal end of the spur gear 70 and the distal rotating shaft 69. Both the rotating shafts 68 and 69 are encased by corresponding flanges 71 and 72 of the rectangular frame 73. The flanges 71 and 72 are configured with a rolling-element bearing joint to reduce rotational friction of the rotating shafts. The outer surface of said gear shaft 70 is configured to mesh with the cylindrical spur gear 51 of the cylindrical gear complex of the upper transverse parallel shaft gear assembly of FIG. 7A.

As depicted in FIG. 8C, a lower lever 87 of a pivoting handle assembly 85~87 with a rack 88 of a rack and pinion assembly is fixedly attached to a proximal lateral sidewall 74 of the longitudinally rectangular frame. A second rack 89 of the other rack and pinion assembly is attached to the opposite lateral sidewall. The pivoting handle assembly is provided in one or a plurality of configurations, including a configuration of a squeezable planar clip which comprises an upper lever 86 pivotably joined the lower lever 87 about a midway toward a proximal end 85. The proximal end 85 is configured to circumferentially and reversibly fasten and unfasten the transverse axial shaft 46 and is secured laterally by the flange 49. The proximal end of the pivoting handle assembly opens on squeezing both the upper 86 and lower levers 87 and closes upon releasing both the levers. The proximal end 85 in a closed configuration fastens and said proximal end 85 in an open configuration unfastens the transverse axial shaft 46. Both the racks 88 and 89 mesh with a pair of passive pinions 90 and 91 which are placed in the corresponding slots 33 and 32, respectively, as illustrated in FIG. 6. One of the pinons, 90, in this particular example, serves as a rotary position sensor that is water-proof, registers curvilinear displacements of the rack 88 and relays position information of the rack to the power and electronic control assembly.

The longitudinally rectangular frame 73 shown in FIG. 8C is configured as an open rectangular box 83 which is limited proximally by a proximal sidewall 75 and distally by a distal sidewall 76. In each inner longitudinal sidewall of the open rectangular box 83, a longitudinal rail slot 84 is carved, which slidably carries the lower horizontal slide rails 63 of the propulsion block to and fro. The upper slide rail 64 of the propulsion block slides to and fro longitudinally on an upper surface of the rectangular frame 73. A proximal portion of said frame comprises a pair of vertical notches 77 and 78 and a pair of recesses 79 and 80 on lateral sidewalls to releasably secure a proximal portion of the invasive device assembly. A distal portion of said frame has a pair of recesses 81 and 82 on lateral sidewalls to releasably secure a distal portion of the invasive device assembly.

FIG. 9 shows a schematic example of individual components of the pivoting handle assembly of the present invention. FIG. 9A shows an exploded view of the assembly. The upper lever comprises a semi-circularly curved-in proximal end 93, a mid-portion 92 and a distal portion 94. On an undersurface of the upper lever, there is provided a pair of knuckles 95 and 96 which are coaxially aligned with a pair of similarly configured knuckles 101 and 102 of the lower lever. In between of said knuckles 95 and 96, a spring band 106~107 is rotatably secured by a pin 105 that is slidably inserted through said knuckles. The spring band provides an outward force separating both the distal portions of the upper and lower levers. The upper lever is unattached to the lateral sidewall of the propulsion assembly and freely movable. The lower lever comprises a semi-circularly curved-in proximal end 98, a mid-portion 97 and a distal portion 99. Both the upper and lower proximal ends 93 and 98 are configured to fasten the cylindrical transverse axial shaft 46. There is provided a thin tubular elastomer 104 slidably inserted over the transverse axial shaft 46, which provides friction between said transverse axial shaft and said proximal ends 93 and 98 upon getting fastened by said proximal ends. The flange 49 caps the transverse axial shaft and prevents slippage and misalignment of the upper proximal end 93. The lower lever is fixedly attached to the outer surface of the lateral side wall 74 of the propulsion assembly, as illustrated in FIG. 8, and is immobile. The rack 88 is provided in one or a plurality of configurations, including a vertically curvilinear configuration, and comprises a horizontal row of gear teeth 103 on an anterior edge of said rack and an adjoining portion 100 on an upper portion of said rack. The gear teeth 103 mesh with the passive pinion 90 and the adjoining portion 100 fixedly adjoins a portion of the lateral sidewall 74 of the propulsion assembly and the distal portion 99 of the pivoting handle assembly.

Figure 10B:
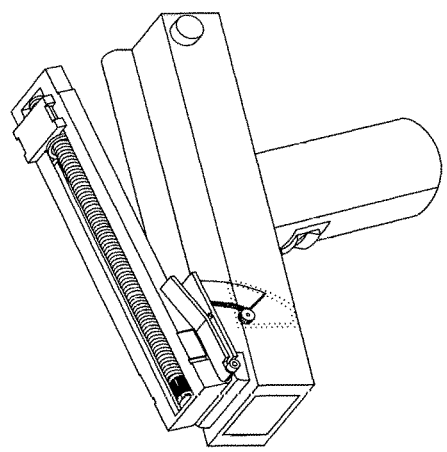
FIG. 10B illustrates an angulated propulsion assembly relative to the longitudinal axis of the apparatus.
Figure 10A:
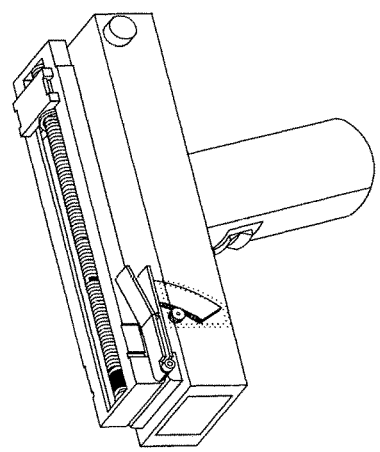
FIG. 10A shows a parallel configuration of the propulsion assembly with the principal enclosure along a longitudinal axis of the apparatus.

FIG. 10 shows a schematic illustrative example of angulation of the propulsion assembly relative to the principal enclosure according to the present invention. FIG. 10A shows a parallel configuration of the propulsion assembly with the principal enclosure along a longitudinal axis of the apparatus. As depicted in FIG. 10B and referring to FIG. 9, the pivoting handle assembly pivots about the transverse axial shaft of the upper transverse parallel shaft gear assembly, which radially rotates the propulsion assembly relative to the longitudinal axis of the principal enclosure.

FIG. 11 shows a schematic illustration of an example of a galvanometer-type electromagnetic pointing device of the present invention, which comprises a set of semi-circular electromagnetic windings 108 circumferentially surrounding a pivoting wire core 109 illustrated in FIGS. 11A and 11B. Both the electromagnetic windings 108 and pivoting wire core 109 are electrically insulated and connected to the power and electronic control assembly of the apparatus. A pair of rotating centers 110 and 111 of each corresponding outer transverse surface of the pivoting wire core 109 are fixedly connected to a pair of corresponding longitudinal levers 112 and 114 located on each side of said pivoting wire core. Near a proximal end of both the longitudinal levers 112 and 114, a pair of symmetrically-arranged vertically curvilinear rails 113 and 115 project in upward and downward directions equidistantly from said longitudinal levers. One end of a linear pointer 116 adjoins the proximal end of the longitudinal lever 112 and the other opposite end of said linear pointer 116 adjoins the proximal end of the other longitudinal lever 114. The linear pointer 116 is configured to block off a part of ultrasound waves transmitted from an ultrasound transducer to a tissue.

FIG. 11C illustrates a schematic example of a placement of the galvanometer-type electromagnetic pointing device enclosed inside a rectangular tubular frame that is made of two transverse rectangular tubular columns 125 and 126 and two longitudinal rectangular tubular columns 127 and 128. The rectangular tubular frame is made of substantially ultrasound-transparent polymer(s) and filled with an electrically non-conductive and ultrasound-transparent liquid and leak-proof. A proximal transverse rectangular tubular column 125 is bordered anteriorly by an outer wall 117 and posteriorly by an inner wall 121 of said tubular column 125. Similarly, a distal transverse rectangular tubular column 126 is bordered anteriorly by an inner wall 122 and posteriorly by an outer wall 118 of said tubular column 126. A longitudinal axis of both the electromagnetic windings 108 and pivoting wire core 109 is aligned in parallel with a transverse axis of said distal transverse tubular column 126. A longitudinal axis of the linear pointer 116 is aligned in parallel with a transverse axis of the proximal transverse tubular column 125 and moves from one side to the other side of said proximal transverse tubular column 125, driven by radial movement of the pivoting wire core 109. The longitudinal axis of the linear pointer 116 is configured to be aligned either in parallel with or at a right angle to a linear axis of an ultrasound transducer array of an ultrasound transducer. The proximal transverse tubular column 125 is configured in a flat rectangular shape located proximal to a proximal end of the ultrasound transducer and is substantially ultrasound-transparent. One longitudinal tubular column 127 is bordered by an inner wall 123 and an outer wall 119 and the other tubular column 128 by an inner wall 124 and an outer wall 120. All four tubular columns 125~128 are bordered by an upper wall and a bottom wall, which seals off said tubular columns. An inner tubular space of each rectangular tubular column is communicated with an inner tubular space of adjoining rectangular tubular columns. A pair of curvilinear slots 129 and 130 located in the longitudinal tubular columns 127 and 128, respectively, provide said curvilinear rails 115 and 113 with a slidable space. The curvilinear slots 113 and 115 are configured to absorb vibrations of the longitudinal levers 112 and 114.

FIG. 12 depicts a schematic illustration of components housed in the principal enclosure of the apparatus according to the present invention. A non-reusable solid gel couplant 133 slidably is placed in front of the rectangular tubular frame 132 enclosing the electromagnetic pointing device, which contacts with a skin overlying a tissue object. Referring to FIG. 11, the rectangular tubular frame 132 encloses an ultrasound transducer in an open box 131 formed by inner walls 121~124 of said tubular columns and aligns longitudinal and transverse axes of said rectangular tubular frame with longitudinal and transverse axes of the ultrasound transducer, respectively. A second solid gel couplant 134 is placed in between of the inner wall 121 of the proximal transverse tubular column 125 and the proximal end of an ultrasound transducer 135, which allows unimpeded transmission of ultrasound waves from the transducer 135 to the proximal transverse tubular column 125. The transducer 135 is configured to be electrically connected to a main ultrasonographic machine through electric cables housed in a handle portion 136 attached to a bottom of said transducer. The electronic control assembly 137 having an integrated circuit board with a segment digital display is placed in the distal portion of the principal enclosure.

FIGS. 13A-13C depict a schematic illustration of an example of a method of coordination of an angular rotation of the invasive tubular device frame 138 together with the propulsion assembly with a horizontal movement of the linear movable pointer 116 of the positioning assembly to aim at a tissue object 139. The linear movable pointer 116 is connected to the longitudinal lever 112 that is configured to rotate about the rotating center 110 coaxially surrounded by the electromagnetic winding 108. The positioning assembly is configured to coordinate pivotable angulation of the invasive tubular device frame 138 about a pivoting center 145 corresponding to the transverse axial shaft 46 shown in FIG. 7D with horizontal movement of the linear movable pointer 116 so as to have a longitudinal axis 144 of the invasive tubular device frame 138 cross a tissue object 139. In FIGS. 13A-13C, upper drawings represent a schematic top-down view of the electromagnetic pointing device showing the linear movable pointer 143 corresponding to the linear movable pointer 116. Mid drawings show a schematic profile view of the apparatus placed atop a skin overlying the tissue object 139. Lower drawings depict a schematic ultrasonographic two-dimensional view 140 seen in a monitor of an ultrasonographic machine. As illustrated in FIG. 13A, once the apparatus is placed on the skin above the tissue object 139, the linear movable pointer 116 generates a linear shadow 142 in the two-dimensional view 140 by blocking off transmissible ultrasonographic waves. In this example, the linear shadow 142 is seen away in a distance from an ultrasonographic image 141 of the tissue object 139. In FIG. 13B, based on a vertical distance 148 from an ultrasound transducer face 147 to the tissue object 139, the invasive tubular device frame 138 is rotated about the pivoting center 145 to an angle 146, enabling the longitudinal axis 144 of said invasive tubular device frame 138 to cross the tissue object 1139. The rotation of said invasive tubular device frame 138 by manually rotating the pivoting handle assembly of FIG. 10B electronically translates into a horizontal movement of the linear movable pointer 116 to a position vertically linear up from the tissue object 139, which is monitored real-time in the two-dimensional ultrasonographic view 140. A crossing of the linear shadow 142 through the tissue object 141 indicates a crossing of the longitudinal axis 144 of the invasive tubular device frame 138 through the tissue object 139. FIG. 13C shows an example of a more acute angle 151 of the invasive tubular device frame 138 calculated from a shorter vertical distance 149 between the tissue object 150 and the ultrasound transducer face 147 while the linear shadow 152 moves the same distance as in FIG. 13B, illustrating an effect of vertical distance between the ultrasound transducer face and the tissue object on angulation of the invasive tubular device frame.

It is to be understood that the aforementioned description of the invasive device positioning assembly and methods of use is simple illustrative embodiments of the principles of the present invention. Various modifications and variations of the description of the present invention are expected to occur to those skilled in the art without departing from the spirit and scope of the present invention. Therefore the present invention is to be defined not by the aforementioned description but instead by the spirit and scope of the following claims.

What is claimed is:

1. An invasive device positioning assembly, comprising:
a position alignment assembly, a pivoting assembly, and a power and electronic control assembly;
the position alignment assembly, wherein the positioning alignment assembly comprises an electromagnetic pointing device and a rotary position sensor, wherein the position alignment assembly is configured to electronically synchronize locating a tissue object in a visualized ultrasonographic field by the position alignment assembly with manually aligning a longitudinal axis of an invasive device assembly reversibly attached to the invasive device positioning assembly with the tissue object, wherein the electromagnetic pointing device is configured to enclose an ultrasound transducer, wherein the electromagnetic pointing device comprises a linear pointer disposed at a proximal end of the electromagnetic pointing device and in front of a proximal end of the ultrasound transducer so as to block transmission of part of ultrasound waves from the ultrasound transducer to the tissue object, wherein the rotary position sensor is rotatably mated with the pivoting assembly, wherein the positioning alignment assembly is configured to provide positional information of the tissue object in relation to the proximal end of the ultrasound transducer, and wherein the position alignment assembly is connected to the power and electronic control assembly;

the pivoting assembly, wherein the pivoting assembly comprises a pivoting handle, a first and second rack and a first and second pinion, wherein the first and second rack mates with the first and second pinion, respectively, wherein the pivoting assembly is rotatably disposed thereof at a proximal portion of the electromagnetic pointing device, wherein the pivoting assembly is configured to pivotably align the longitudinal axis of the invasive device assembly reversibly attached to the invasive device positioning assembly with the tissue object, and wherein the pivoting assembly is configured to be manually pivotable about a pivoting center disposed thereof at a proximal portion of the invasive device assembly; and the power and electronic control assembly, wherein the power and electronic control assembly comprises an integrated circuit board, a control knob connected to the integrated circuit board and a battery, and wherein the power and electronic control assembly is configured to electronically synchronize locating the tissue object in a visualized ultrasonographic field by the position alignment assembly with manually aligning a longitudinal axis of an invasive device assembly reversibly attached to the invasive device positioning assembly with the tissue object.

2. The invasive device positioning assembly according to claim 1, wherein the electromagnetic pointing device comprises:

electromagnetic windings, a pivoting wire core, a pair of longitudinal levers, the linear pointer and an electromagnetic pointing device enclosure;

the electromagnetic windings, wherein the electromagnetic windings are located distally to the ultrasound transducer, wherein a longitudinal axis of the electromagnetic windings is aligned in parallel with a transverse axis of the ultrasound transducer, and wherein the electromagnetic windings are configured to coaxially and reversibly rotate the pivoting wire core encircled by the electromagnetic windings;

the pivoting wire core, wherein the pivoting wire core is coaxially and rotatably encircled by the electromagnetic windings, wherein a longitudinal axis of the pivoting wire core is aligned in parallel with the transverse axis of the ultrasound transducer, wherein a rotating center located thereof at each lateral end of the pivoting wire core is fixedly connected to a distal end of the longitudinal lever, wherein the pivoting wire core is configured to controllably rotate about the longitudinal axis of the electromagnetic windings, and wherein the controllable rotation of the pivoting wire core is configured to be synchronized with the manual alignment of the longitudinal axis of the invasive device assembly reversibly attached to the invasive device positioning assembly with the tissue object;

the longitudinal lever, wherein the longitudinal lever is movably housed inside the electromagnetic pointing device enclosure, wherein the distal end of the longitudinal lever is fixedly connected to the rotating center of the each lateral end of the pivoting wire core, wherein a proximal end of the longitudinal lever is fixedly connected to each lateral end of the linear pointer, wherein the longitudinal lever is configured to radially rotate about the rotating center of the pivoting wire core, wherein the longitudinal lever is configured with a rail fixedly connected to the longitudinal lever at a right angle disposed thereof at the proximal end of the longitudinal lever, wherein the rail of the longitudinal lever is configured to mate with a slot disposed on an inner wall of the proximal portion of the electromagnetic pointing device enclosure, and wherein the rail of the longitudinal lever is configured to reduce vibration of the longitudinal lever;

the linear pointer, wherein the lateral end of the linear pointer is fixedly connected at a right angle to the proximal end of the longitudinal lever, wherein the linear pointer is movably housed in the electromagnetic pointing device enclosure in front of the proximal end of the ultrasound transducer, wherein the linear pointer is configured to block the transmission of the part of the ultrasound waves from the ultrasound transducer to the tissue object, and wherein the blocking of the transmission of the part of the ultrasound transducer is configured to produce the linear shadow line in the visualized ultrasonographic field; and the electromagnetic pointing device enclosure, wherein the electromagnetic pointing device enclosure is provided in a configuration of rectangular hollow tubular frame having a rectangular open central space bordered by the rectangular hollow tubular frame, wherein the proximal portion of the electromagnetic pointing device enclosure is configured to house the linear pointer, wherein a distal portion of the electromagnetic pointing device enclosure is configured to house the electromagnetic windings coaxially encircling the pivoting wire core, wherein a lateral portion of the electromagnetic pointing device enclosure is configured to house the longitudinal lever, wherein the slot disposed on the inner wall of the proximal portion of the electromagnetic pointing device enclosure is configured to mate with the rail of the longitudinal lever so as to reduce the vibration of the longitudinal lever, wherein the electromagnetic pointing device enclosure is filled with an ultrasound-transparent and electrically non-conductive liquid, wherein the electromagnetic pointing device enclosure is configured to be leak-proof, and wherein the electromagnetic pointing device enclosure is configured to encircle the ultrasound transducer reversibly disposed inside the rectangular open central space of the electromagnetic pointing device enclosure.

3. The invasive device positioning assembly according to claim 1, wherein the pivoting handle comprises:

wherein the pivoting handle is provided in a reversibly clampable configuration having a pivotable upper lever and an immobile lower lever;

the pivotable upper lever, wherein the pivotable upper lever comprises a reversible clamp portion at a proximal portion of the pivotable upper lever, a pivotable portion disposed thereof at a mid portion of the pivotable upper lever and a distal portion, wherein the pivotable upper lever is configured to be pivotably connected with the immobile lower lever thereof at the pivotable portion of the pivotable upper lever, wherein the reversible clamp portion of the pivotable upper lever is configured to pivotably mate with a reversible clamp portion of the immobile lower lever at a proximal portion of the immobile lower lever so as to reversibly fasten the pivoting center disposed thereof at the proximal portion of the invasive device assembly; and the immobile lower lever, wherein the immobile lower lever comprises the reversible clamp portion at the proximal portion of the immobile lower lever, a mid portion and a distal portion, wherein the immobile lower lever is to fixedly attached to a side wall of the invasive device assembly, wherein the mid portion of the immobile lower lever is configured to mate with the pivotable portion of the pivotable upper lever, wherein the distal portion of the immobile lower lever is fixedly attached to the first rack of the pivoting assembly, wherein pivotably rotating the immobile lower lever about the pivoting center disposed thereof at the proximal portion of the invasive device assembly is configured to align the longitudinal axis of the invasive device assembly reversibly attached to the invasive device positioning assembly with the tissue object.

4. The invasive device positioning assembly according to claim 1, wherein the pivoting assembly further comprise:

the first rack, wherein the first rack of the pivoting assembly is provided in a vertically curvilinear configuration, wherein the first rack comprises a top portion of the first rack and a set of gear teeth disposed on an anterior surface of the first rack, wherein the top portion of the first rack is fixedly attached to an undersurface of the invasive device assembly thereof at a first side wall of the invasive device assembly, wherein the first rack is fixedly attached to the distal portion of the immobile lower lever of the pivoting handle, and wherein vertical curvilinear rotation of the first rack is configured to be coordinated with the pivotable rotation of the immobile lower lever about the pivoting center disposed thereof at the proximal portion of the invasive device assembly;

the second rack, wherein the second rack of the pivoting assembly is provided in the vertically curvilinear configuration, wherein the second rack comprises a top portion of the second rack and a set of gear teeth disposed on an anterior surface of the second rack, wherein the top portion of the second rack is fixedly attached to the undersurface of the invasive device assembly thereof at a second side wall of the invasive device assembly, and wherein vertical curvilinear rotation of the second rack is configured to be coordinated with the vertical curvilinear rotation of the first rack;

the first pinion, wherein the first pinion comprises a circular gear having the rotary position sensor of the position alignment assembly, wherein the circular gear is configured to coaxially adjoin the rotary position sensor of the position alignment assembly at a rotating center of the first pinion, wherein the first pinion is configured to mesh with the first rack so as to be passively rotated by the first rack, and wherein rotation of the first pinion by the vertical curvilinear rotation of the first rack is configured to generate electronic information of rotational displacement of the invasive device assembly by the rotary position sensor; and the second pinion, wherein the second pinion comprises a circular gear, wherein the second pinion is configured to mesh with the second rack so as to be passively rotated by the second rack, and wherein rotation of the second pinion is configured to be coordinated with the rotation of the first pinion so as to stabilize the vertical curvilinear rotation of the rack.

5. A method of aligning an invasive device with a tissue object in a visualized ultrasonographic field, comprising:

providing an invasive device positioning assembly comprising a position alignment assembly, a pivoting assembly, and a power and electronic control assembly;

assembling the invasive device positioning assembly with an ultrasound transducer, wherein the ultrasound transducer is reversibly enclosed in an electromagnetic pointing device enclosure, and wherein a face of the ultrasound transducer is placed distal to a proximal end of an electromagnetic pointing device;

assembling the invasive device positioning assembly with an invasive device assembly, wherein a pivoting assembly of the invasive device positioning assembly is configured to be assembled with a pivoting center disposed thereof at a proximal portion of the invasive device assembly, and wherein the pivoting center disposed thereof at the proximal portion of the invasive device assembly is circumferentially fastened by a reversible clamp portion of a pivoting handle of the pivoting assembly;

placing an invasive device in the invasive device assembly;

powering up the power and electronic control assembly of the invasive device positioning assembly and the ultrasound transducer;

visualizing a tissue object in an visualized ultrasonographic field by placing the proximal end of the electromagnetic pointing device on a skin overlying the tissue object and by scanning the tissue object by the ultrasound transducer;

generating a linear shadow line in the visualized ultrasonographic field showing a tissue area surrounding tissue object, wherein the linear shadow line is produced by blocking transmission of part of ultrasound waves emitted from the ultrasound transducer to the tissue area surrounding the tissue object by a linear pointer disposed thereof at the proximal end of the electromagnetic pointing device, and wherein the linear pointer is configured to be in parallel with one transverse axis of the proximal end of the electromagnetic pointing device;

unfastening the pivoting center disposed thereof at the proximal portion of the invasive device assembly by loosening the reversible clamp portion of the pivoting handle of the pivoting assembly, wherein the reversible clamp portion of the pivoting handle is configured to be loosened by manually depressing a distal portion of a pivotable upper lever of the pivoting handle toward a distal portion of an immobile lower lever of the pivoting handle;

pivotably rotating the invasive device assembly about the pivoting center disposed thereof at the proximal portion of the invasive device assembly by pivotably rotating the immobile lower lever about the pivoting center disposed thereof at the proximal portion of the invasive device assembly, wherein the immobile lower lever is fixedly attached to a side wall of the invasive device assembly;

synchronizing the pivotable rotation of the invasive device assembly with aligning the linear shadow line with the tissue object in the visualized ultrasonographic field, wherein the pivotable rotation of the invasive device assembly is electronically measured for rotational displacement of the invasive device assembly by a rotation position sensor coaxially disposed with a first pinion of the pivoting assembly, wherein electronic information of the rotation displacement of the invasive device assembly is processed by the power and electronic control assembly, wherein the power and electronic control assembly is configured to controllably rotate a pivoting wire core encircled by electromagnetic windings of the electromagnetic pointing device, wherein a distal end of a longitudinal lever of the electromagnetic pointing device is fixedly connected to a lateral end of the pivoting wire core, wherein a proximal end of the longitudinal lever of the electromagnetic pointing device is fixedly connected to a lateral end of the linear pointer of the electromagnetic pointing device, wherein the electromagnetic windings encircling the pivoting wire core is located distal to a distal end of the ultrasound transducer, wherein the longitudinal lever of the electromagnetic pointing device is configured to be in parallel with a longitudinal axis of the ultrasound transducer, and wherein the electromagnetic pointing device is housed in a leak-proof enclosure filled with an ultrasound-transparent and electrically non-conductive liquid; and fastening the pivoting center disposed thereof at the proximal portion of the invasive device assembly by releasing the distal portion of the pivotable upper lever of the pivoting handle from the distal portion of the immobile lower lever of the pivoting handle, wherein the fastening of the pivoting center disposed thereof at the proximal portion of the invasive device assembly is synchronized with crossing an ultrasonographic image of the tissue object by the linear shadow line produced by the linear pointer of the electromagnetic pointing device in the visualized ultrasonographic field, and wherein a longitudinal axis of the invasive device is configured to be aligned at an angle with the tissue object by the synchronization of the fastening of the pivoting center disposed thereof at the proximal portion of the invasive device assembly with the crossing of the ultrasonographic image of the tissue object by the linear shadow line produced by the linear pointer of the electromagnetic pointing device.

\* \* \* \* \*